United States Patent [19]
Sekizawa et al.

[11] Patent Number: 4,914,247
[45] Date of Patent: Apr. 3, 1990

[54] PROCESS FOR PREPARING PARA-SUBSTITUTED HALOGENOBENZENE DERIVATIVES

[75] Inventors: Kazuhiko Sekizawa, Shinnanyo; Toshio Hironaka, Tokuyama; Masao Nakano, Hikari; Yukihiro Tsutsumi, Tokuyama, all of Japan

[73] Assignee: Toyo Soda Manufacturing Co., Ltd., Shinnanyo, Japan

[21] Appl. No.: 374,578

[22] Filed: Jun. 30, 1989

Related U.S. Application Data

[63] Continuation of Ser. No. 9,346, Jan. 30, 1987, abandoned.

[30] Foreign Application Priority Data

Jan. 31, 1986 [JP] Japan ................................ 61-19693

[51] Int. Cl.4 .............................................. C07C 17/12
[52] U.S. Cl. .................................... 570/208; 570/190; 570/206; 570/207
[58] Field of Search ................ 570/190, 206, 207, 208

[56] References Cited

U.S. PATENT DOCUMENTS 4,530,824  7/1985  Arika et al. ........................ 423/328
4,754,086  6/1988  Higuchi et al. .................... 570/208
4,822,933  4/1989  Suzuki et al. ..................... 570/208

FOREIGN PATENT DOCUMENTS 0112722   4/1984  European Pat. Off. ............. 570/208
0118851   9/1984  European Pat. Off. ............. 570/208
0141514   5/1985  European Pat. Off. .
0154236   9/1985  European Pat. Off. ............. 570/206
0171265   2/1986  European Pat. Off. ............. 570/206
0195514   9/1986  European Pat. Off. ............. 570/208
0231133   8/1987  European Pat. Off. ............. 570/208
59-144722 8/1984  Japan .
1171444   8/1986  Japan ................................ 570/208

OTHER PUBLICATIONS

T. Wortel et al., "Selective Bromination of Halobenzenes Using Zeolite Catalysts," J. of Catalysis 60, pp. 110–120 (1979).
T. Huizinga, "Zeolite ZSM-5 and Related Materials as Catalyst in Benzene Chlorination," Tetrahedron Letters 21, pp. 3809–3812 (1980).

Primary Examiner—Werren B. Lone
Attorney, Agent, or Firm—Cushman, Darby & Cushman

[57] ABSTRACT

A para-substituted halogenobenze derivative is prepared by halogenating a benzene derivative in the liquid phase in the presence of a molded zeolite catalyst body comprising, based on the weight of the molded zeolite catalyst body, 10 to 95% by weight of an L-type zeolite as the anhydrous state and 5 to 90% by weight of amorphous silica.

12 Claims, 1 Drawing Sheet

PROCESS FOR PREPARING PARA-SUBSTITUTED HALOGENOBENZENE DERIVATIVES

BACKGROUND OF THE INVENTION

This is a continuation of application Ser. No. 009,346, filed Jan. 30, 1987, which was abandoned upon the filing hereof.

(1) Field of the Invention

The present invention relates to a process for preparing a halogenobenzene derivative by halogenating a benzene derivative in the liquid phase. More particularly, it relates to a process for preparing a parasubstituted halogenobenzene derivative by halogenating a benzene derivative in the liquid phase in the presence of a molded zeolite catalyst body comprising an L-type zeolite and amorphous silica.

(2) Description of the Related Art

Halogenobenzene derivatives are important intermediates in the fields of medicines and agricultural chemicals and the field of organic synthesis and these halogenobenzene derivatives are ordinarily prepared by halogenating benzene derivatives in the liquid phase in the presence of a Lewis acid, for example, ferric chloride or antimony chloride, as the catalyst. For example, dichlorobenzene (hereinafter referred to as "DCB") is prepared by blowing chlorine gas into benzene or monochlorobenzene (hereinafter referred to as "MCB").

In the production of a di-substituted benzene derivative by the liquid phase halogenation of a mono-substituted benzene derivative, three isomers, that is, a 1,2-di-substituted compound (ortho-compound), a 1,3-substituted compound (meta-compound) and a 1,4-di-substituted compound (para-compound), are obtained as products, and it is known that the ratio in the amount of these isomers is determined according to the kind of the substituent present in the starting benzene derivative, the kind of the catalyst, and other factors. For example, when DCB is prepared by the liquid phase chlorination of MCB in the presence of ferric chloride, the ratio in the amount of the three isomers is as follows.

o-Dichlorobenzene: 30 to 40%
m-Dichlorobenzene: 0 to 5%
p-Dichlorobenzene: 60 to 70%

From the industrial viewpoint, the parasubstituted halogenobenzene derivative is most important among the three isomers, and the demand for the parasubstituted halogenobenzene derivative is largest. Accordingly, various processes for selectively preparing parasubstituted halogenobenzene derivatives have been proposed.

Of these conventional processes, there can be mentioned a process for selectively preparing a parasubstituted halogenobenzene derivative by halogenating a benzene derivative in the presence of a zeolite as the catalyst. For example in the Journal of Catalysis, 60, 110 (1979), it is reported that a zeolite can be used as the catalyst for the bromination of a halogenobenzene. Furthermore, in Tetrahedron Letters, 21, 3809 (1980), it is reported that ZSM-5, ZSM-11, mordenite. L-type zeolite, and Y-type zeolite can be used as the catalyst for the chlorination of benzene, and it is taught that an especially high selectivity to p-dichlorobenzene (hereinafter referred to as "PDCB") is obtained when an L-type zeolite is used. Moreover, processes for the halogenation of benzene or alkylbenzenes using an L-type zeolite or Y-type zeolite as the catalyst are disclosed in Japanese Unexamined Patent Publications No. 59-130227, No. 59-144,722, and No. 59-163,329. However, in these known literature references, only the catalytic properties of the zeolites per se are described.

Moreover, Japanese Unexamined Patent Publication No. 60-109,529 discloses a process in which mixture of dialkylbenzenes rich in the para-dialkylbenzene isomer is prepared by subjecting an alkylbenzene to the alkylation reaction in the presence of a composite catalyst comprising a matrix composed of a crystalline aluminosilicate having a silica/alumina ratio of at least 12 and a constraint index of 1 to 12, such as ZSM-5, and substantially amorphous silica. In this prior art reference, it is taught that the zeolite component is ion-exchanged to a proton type and is used for the alkylation reaction or the like.

From the prior art techniques, it is obvious that zeolites have an effective catalytic action for the halogenation of benzene derivatives. However, since zeolites are ordinarily obtained in the form of crystalline fine powders, the zeolites are seldom used directly as practical catalysts or industrial catalysts.

In general, where the catalyst component is powdery, if it is directly used in the powdery state, a pressure loss occurs and separation or recovery of the catalyst becomes necessary to avoid incorporation of the powdery catalyst into the product. Accordingly, to avoid these disadvantages, the catalyst is molded into an appropriate shape and size, such as a spherical or columnar pellet or a granule according to the mode of use of the catalyst, for example, a fixed bed, a suspended bed or a fluidized bed, the reaction mode, for example, a batchwise reaction or a continuous reaction, and the state of use of the catalyst, for example, the type of a reaction vessel. On the other hand, the stability or durability of the catalyst under application conditions, that is, the catalyst life in a broad sense, is a very important factor. Accordingly, in the case of a molded catalyst body, high mechanical strength characteristics such as high hardness and high abrasion resistance are required, and when the powdery catalyst is molded, the catalyst is required to exhibit a good moldability inclusive of a high molding efficiency. Therefore, when the powdery catalyst component is molded, a binder is ordinarily added to improve the moldability and the mechanical strength of the obtained molded catalyst body.

The zeolite powder is non-caking and has a poor moldability. Accordingly, an inorganic compound other than the zeolite, such as alumina or silica alumina, is often used as the binder for molding the zeolite powder. However, the binder added for improving the moldability sometimes has a bad influence on the catalytic reaction, and therefore, where binder-containing catalyst is used, it is often difficult to obtain the same activity and selectivity as attainable when a zeolite powder per se is used as the catalyst. The bad influence of the binder in the binder-containing zeolite catalyst depends greatly on the kind of the chemical reaction for which the catalyst is used and the kind of the zeolite component in the catalyst, and furthermore, the mechanical strength of the catalyst is changed according to the kinds of the binder and the zeolite component. Consequently, an appropriate molded zeolite catalyst body is necessary for the particular chemical reaction according to the state of use of the catalyst.

Therefore, also in the liquid phase halogenation of a benzene derivative in the presence of a zeolite catalyst, development of a molded zeolite catalyst body having an industrially applicable mechanical strength, in which the performance of the zeolite powder per se, such as catalytic activity and selectivity, are not reduced, is eagerly desired.

Under this background, we carried out research with a view to developing practically applicable zeolite catalyst for the catalytic halogenation of benzene derivatives.

As the result, it was found that if a molded zeolite catalyst body composed solely of L-type zeolite is used, a high yield of a para-substituted halogenobenzene derivative is obtained, but since the mechanical strength is low, pulverization, abrading or powdering occurs under application conditions to render stationary continuation of the reaction difficult, and the powder of the catalyst is incorporated in the product. It also was found that, if alumina or silica-alumina is used as the binder in combination with L-type zeolite, the mechanical strength is improved, but the selectivity to a para-substituted halogenobenzene derivative is drastically reduced and these catalysts are not preferred from the industrial viewpoint.

SUMMARY OF THE INVENTION

In view of the foregoing, it is the primary object of the present invention to provide a molded zeolite catalyst body showing a high yield of a para-substituted halogenobenzene derivative in the liquid phase halogenation of a benzene derivative and having a high mechanical strength to abrasion or the like.

In accordance with the present invention, there is provided an improved process for preparing a para-substituted halogenobenzene derivative wherein a benzene derivative is halogenated in the liqui phase in the presence of an L-type zeolite catalyst. In this improved process, a molded zeolite catalyst body comprising, based on the weight of the molded zeolite catalyst body, 10 to 95% by weight of an L-type zeolite as the anhydrous state and 5 to 90% by weight of amorphous silica.

DESCRIPTION OF THE PREFERRED EMBODIMENTS

Figure 1:
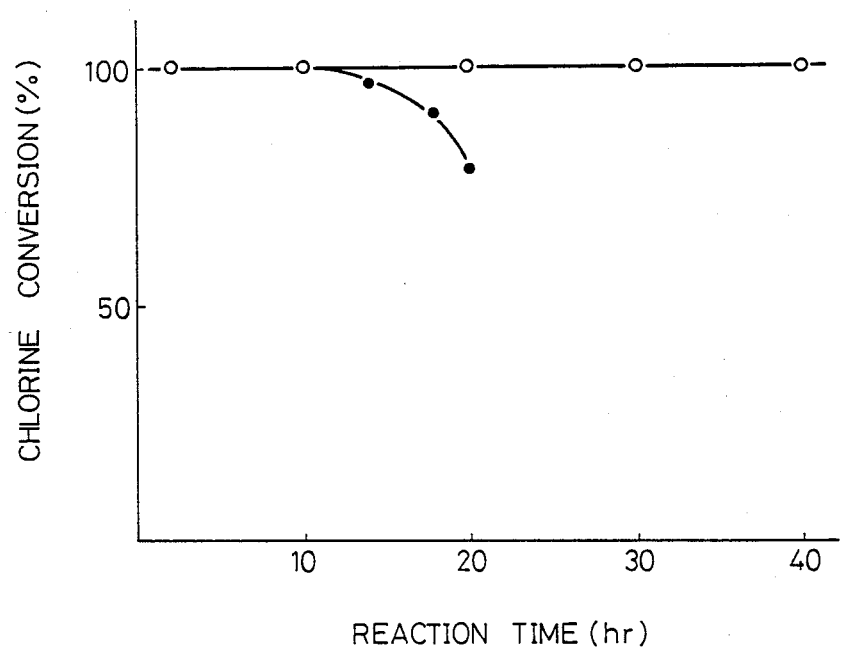
FIG. 1 is a graph showing the change of the chlorine conversion in the continuous liquid phase chlorination of MCB according to the process of the present invention using catalyst A and according to the comparative process using catalyst H.

The present invention will now be described in detail.

In the present invention, the zeolite component of the molded zeolite catalyst body is an L-type zeolite.

Since an L-type zeolite has a characteristic crystal structure, it can be distinguished from other zeolites by the powder X-ray diffractometry. L-type zeolite is a kind of a synthetic zeolite and can be synthesized according to a known process. In the present invention, the process for the synthesis of an L-type zeolite is not particularly critical. A typical composition of an L-type zeolite is represented by the following oxide molar ratio formula:

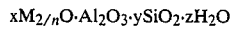

wherein M is a cation, n is a valency of the cation M, x is a number of 0.7 to 1.3, y is a number of 4 to 8, and z is a number varying depending upon the extent of hydration of the zeolite and is ordinarily from 0 to 9. A typical example of the L-type zeolite has a composition expressed by the following oxide molar ratio formula:

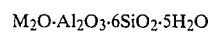

wherein M is sodium and/or potassium.

The as-prepared L-type zeolite can be used as the catalyst, but all or a part of the metal cation (M) contained in the as-prepared L-type zeolite may be ion-exchanged with another metal cation and/or proton before it is used as the catalyst. The ion exchange treatment may be accomplished according to known procedures, for example, by suspending the zeolite in an aqueous solution containing the intended metal cation and stirring the suspension at 20° C. to 100° C. for 1 to 50 hours.

In the L-type zeolite used in the process of the present invention, preferably at least 30%, especially at least 60%, of the exchange ion sites is occupied by an alkali metal cation.

The second indispensable component of the molded zeolite catalyst body used in the process of the present invention is amorphous silica. Amorphous silica has no crystal structure, and in this point, amorphous silica is different from quartz, tridymite, cristobalite and the like. Namely, a compound substantially solely of silica in terms of the anhydrous state is meant. The process for the synthesis of amorphous silica is not particularly critical. For example, silica gel synthesized from silica sol can be used.

In the molded zeolite catalyst body used in the process of the present invention, the ratio between the zeolite component and amorphous silica may be changed, but the content of the zeolite component is 10 to 95% by weight as the anhydrous state and is preferably 40 to 90% by weight. If the content of the zeolite component is lower than 10% by weight, the rate of the halogenation reaction is reduced, and if the content of the zeolite component exceeds 95% by weight, the function of amorphous silica as the binder becomes unsatisfactory and the mechanical strength of the molded zeolite catalyst body is reduced.

In the process of the present invention, a mixture of the zeolite component and amorphous silica is molded and the resulting molded zeolite catalyst body is used. The method for mixing the zeolite component with amorphous silica is not particularly critical and a method in which both the components are mixed physically and sufficiently may be adopted without limitation. For example, a mixture of the zeolite component and amorphous silica is prepared by adding silica sol to an aqueous suspension of the zeolite component, sufficiently stirring the dispersion, and removing water by evaporation. The method for molding the mixture of the zeolite component and amorphous silica is not particularly critical, and there may be adopted ordinary methods such as an extrusion molding method, a compression molding method, a spray-drying granulation method, and a rolling granulation method. When the mixture of the zeolite component and amorphous silica is prepared, organic materials such as polyvinyl alcohol, stearic acid and starch may be added to ease the mixing and molding operations and to improve the pore structure of the molded catalyst, if desired.

In the process of the present invention, the mechanical strength of the molded zeolite catalyst body is important, and the mechanical strength can be expressed by the abrasion ratio. The abrasion ratio referred to herein is determined from the results of the abrasion test described below and is a criterion indicating the mechanical strength of the molded catalyst body to the abrasion.

Stainless steel sieves having a diameter of 20 cm and mesh sizes of 105 μm and 74 μm, respectively, are piled on a pan so that the sieve having a larger mesh size is located above. Then, 50 g of a molded zeolite body classified to 105 μm to 250 μm in advance is evenly placed on the sieve having a mesh size of 105 μm. Then, five copper pieces having a diameter of 23 mm and a thickness of 1.5 mm are arranged on the molded zeolite body, and the piled sieves are violently shaken by a shaker for 15 minutes. The portion of the molded zeolite body which has been abraded, powdered, passed through the sieve having a mesh size of 74 μm, and collected on the pan is weighed. The abrasion ratio is calculated from the amount of the powder collected on the pan according to the following equation:

$$\text{Abrasion ratio (\%)} = \frac{\text{amount (g) of powder collected in pair}}{50 \text{ (g)}} \times 100$$

If the size of the molded zeolite body is larger than 250 μm, the abrasion test is carried out after pulverization. If the size of the molded body is smaller than 105 μm, the abrasion test is similarly carried out by using sieves having a smaller mesh size.

If the liquid phase halogenation is carried out by using a molded zeolite catalyst body having an abrasion ratio exceeding 30% by weight, abrading or powdering of the molded catalyst body is violent and separation or recovery of the catalyst becomes difficult. Therefore, in the case of the batchwise or semi-batchwise reaction, the catalyst is incorporated into the product, and in the case of the continuous reaction, a bad influence is imposed on the product by the catalyst and stationary continuation of the reaction becomes impossible because of flow-out of the catalyst from the reaction vessel.

After the molding operation, the molded zeolite catalyst body is dried and calcined and is then used for the liquid phase halogenation. Where organic materials are added for the preparation of the molded zeolite catalyst body, the organic materials are expelled from the molded body during calcination. It is sufficient if the calcination treatment is carried out at 300° to 900° C. for 30 minutes to 24 hours. If the calcination temperature is lower than 300° C., the strength of the molded zeolite catalyst body is not increased to a sufficiently high level, and if the calcination temperature is higher than 900° C., the crystal structure of the L-type zeolite is destroyed.

In the process of the present invention, the benzene derivative means benzene and compounds having a structure such that at least one hydrogen atom of benzene is substituted with a halogen atom or an alkyl group, such as halogenobenzenes and alkylbenzenes. As specific examples, there can be mentioned benzene, monofluorobenzene, MCB, monobromobenzene, monoiodobenzene, toluene and ethylbenzene. An elementary halogen is used as the halogenating agent. For example, there can be mentioned chlorine, bromine, and iodine.

In the process of the present invention, the reaction apparatus, reaction procedures, and reaction conditions are not particularly critical, so far as the benzene derivative is in contact in the liquid state with the catalyst. For example, any batchwise, semi-batchwise, and continuous reaction apparatuses can be used. The catalyst is used, for example, in the form of a fixed bed or suspended bed. The reaction may be carried out in the presence of a solvent not participating in the halogenation, for example, carbon tetrachloride. When such a solvent is used, the concentration of the benzene derivative is 5 to 99% by weight, preferably 20 to 99% by weight. If the concentration of the benzene derivative is lower than 5% by weight, the chance of the contact of the starting material with the catalyst is reduced and a sufficient conversion cannot be obtained. If the halogenating agent is continuously supplied, it may be accompanied by an inert gas such as nitrogen, helium or carbon dioxide. If such an accompanying gas is used, the concentration of the halogenating agent is 5 to 99% by volume, preferably 20 to 99% by volume.

Where a batchwise or semi-batchwise reaction apparatus is used, the catalyst is ordinarily used in the state suspended in a solution, and the amount of the catalyst per unit volume of the reaction solution is 0.001 to 1 kg/l, preferably 0.05 to 0.1 kg/l. If the amount of the catalyst is smaller than 0.001 kg/l, the load imposed on the catalyst is too large and a satisfactory conversion can not be obtained. If the amount of the catalyst exceeds 1 kg/l, a further increase of the effect is not attained by the increase of the amount of the catalyst. Where the halogenating agent is continuously supplied, the amount of the halogenating agent supplied can be expressed by the amount of the halogenating agent to the weight of the zeolite per unit hour. Namely, in this case, the amount of the catalyst is 1 to 1500 mol/kg-cat.hr and is preferably 10 to 800 mol/kg-cat.hr. If the amount of the catalyst is smaller than 1 mol/kg-cat.hr, a sufficient rate of formation of the halogenobenzene cannot be obtained. If the amount of the catalyst is larger than 1,500 mol/kg-cat.hr, the amount of the unreacted halogenating agent is increased and the process becomes economically disadvantageous.

Where a continuous reaction apparatus is used, the amount of the starting liquid material supplied can be expressed by the amount to the weight of the zeolite used per unit hour. Namely, in this case, the amount of the starting liquid material supplied is 0.5 to 300 l/kg-cat.hr and is preferably 2 to 100 l/kg-cat hr. Other reaction conditions are the same as those adopted in the case where a batchwise or semi-batchwise reaction apparatus is used.

In the process of the present invention, the reaction temperature and reaction pressure are not particularly critical, so far as the benzene derivative is kept liquid. Even if the reaction temperature is made higher than the boiling point of the benzene derivative, the halogenation reaction can be carried out in the liquid phase by increasing the pressure. However, preferably the reaction temperature is in the range of 0° to 200° C., especially 20° to 150° C. If the reaction temperature is lower than 0° C., a sufficient rate of reaction cannot be obtained. If the reaction temperature is higher than 200° C., the selectivity to the para-substituted halogenobenzene derivative is reduced.

According to the process of the present invention, a para-substituted halogenobenzene derivative which is industrially valuable can be obtained in a high yield by the liquid phase halogenation of a benzene derivative, and since separation and recovery of the catalyst can be easily accomplished and the problem of flow-out of the catalyst does not arise in the case of the continuous reaction, the production can be performed economically advantageously.

The present invention will now be described in detail with reference to the following examples that by no means limit the scope of the invention. In the examples, the conversion and selectivity were determined according to the following equations:

$$\text{Conversion (\%)} = \frac{\begin{pmatrix}\text{amount (mole) of}\\\text{benzene deriv-}\\\text{ative supplied}\end{pmatrix} - \begin{pmatrix}\text{amount (mole) of}\\\text{unreacted benzene}\\\text{derivative}\end{pmatrix}}{\text{amount (mole) of benzene derivative supplied}} \times 100$$

$$\text{Selectivity (\%)} = \frac{\text{amount (mole) of intended product formed}}{\text{total amount (mole) of all of products formed}} \times 100$$

Referential Example

Hydrothermal synthesis of an L-type zeolite was carried out according to the process disclosed in Japanese Unexamined Patent Publication No. 59-73,421, the obtained slurry was filtered, and the recovered solid was sufficiently washed with water and then dried at 110° C. for 15 hours. The obtained solid was found to have the following oxide molar composition:

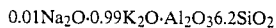
0.01Na$_2$O·0.99K$_2$O·Al$_2$O$_3$·6.2SiO$_2$

From the results of the Cu-K$\alpha$ doublet powder X-ray diffractometry, it was confirmed that the solid was an L-type zeolite.

This powder of the L-type zeolite (having a particle size of 0.1 to 0.5 μm) was calcined at 540° C. for 3 hours under a circulation of air, and by using the calcined product as the catalyst, chlorination of MCB was carried out in the liquid phase in an ordinary semi-batch-wise reaction apparatus. More specifically, 40 g of MCB was charged in a Pyrex glass reaction vessel (inner diameter =40 mm, height =100 mm) having an inner capacity of about 100 ml and equipped with a gas-blowing tube, a condenser, and a stirrer, and 2 g of the L-type zeolite powder was suspended in MCB. While the suspension was sufficiently stirred, chlorine has (accompanied by the same amount of nitrogen gas) was blown into the suspension at a feed rate of 30 ml/min. The reaction temperature was adjusted to 100° C. by controlling the temperature of the periphery of the reaction vessel by an oil bath. When 3 hours had passed from the point of initiation of blowing of chlorine gas, the product was analyzed by the gas chromatography. The obtained results are shown in Table 1.

Example 1

A mixture of 100 parts by weight of an L-type zeolite synthesized in Referential Example, 15 parts by weight (as silica) of silica sol (SiO$_2$ content =30% by weight; supplied by Catal. & Chem. Ind. Co.), and 65 parts by weight of distilled water were sufficiently stirred to form a homogeneous slurry. The slurry was introduced into a spray-drying granulation apparatus and was molded into a granular catalyst. The molded catalyst was calcined at 600° C. for 1 hour under a circulation of air and the calcination product was classified to obtain a catalyst A having a particle size of 105 to 250 μm (105 to 177 μm: 42.3% by weight, 177 to 250 μm: 57.7% by weight). The catalyst A was subjected to the abrasion test, and by using 2.3 g of the catalyst A, the liquid phase chlorination of MCB was carried out in the same manner as described in the Referential Example. The results obtained when 3 hours had passed from the initiation of chlorine gas blowing are shown in Table 1.

Comparative Example 1

A granular catalyst B having a particle size of 105 to 250 μm (105 to 177 μm: 50.6% by weight, 177 to 250 μm: 49.4% by weight) and comprising alumina as the binder was prepared in the same manner as described in Example 1 except that alumina sol (supplied by Nissan Chem. Ind. Ltd.) was used instead of the silica sol used in Example 1. The catalyst B was subjected to the abrasion test, and by using 2.3 g of the catalyst B, the liquid phase chlorination of MCB was carried out in the same manner as described in Example 1. The results obtained when 3 hours has passed from the initiation of chlorine gas blowing are shown in Table 1.

TABLE 1

|  | Referential Example | Example 1 | Comparative Example 1 |
|---|---|---|---|
| Catalyst | Powder | A | B |
| Binder | — | Silica | Alumina |
| Content (%) of L-type zeolite | 100 | 87 | 87 |
| Abrasion ratio (%) | — | 5.1 | 0.8 |
| Conversion (%) of MCB | 67.1 | 66.9 | 67.3 |
| Selectivity (%) to: |  |  |  |
| PDCB | 87.7 | 87.8 | 70.3 |
| ODCB[1] | 11.4 | 11.2 | 27.6 |
| Others[2] | 0.9 | 1.0 | 2.1 |

Note
[1]ODCB: ortho-dichlorobenzene
[2]Others: meta-dichlorobenzene and trichlorobenzenes

Examples 2 through 4

To 250 parts by weight of an aqueous solution of sodium chloride, strontium chloride or ammonium chloride (1 mol/l) was added 30 parts by weight of an L-type zeolite synthesized in Referential Example, and the ion exchange treatment was carried out at 90° C. for 5 hours. The slurry was filtered and the recovered solid was sufficiently washed with water and then dried at 110° C. for 16 hours. The X-ray diffraction period was not substantially different in these ion-exchanged L-type zeolites, and they were found to have oxide molar compositions of 0.43Na$_2$O·0.58K$_2$O·Al$_2$O$_3$·6.1SiO$_2$, 0.33SrO·0.67K$_2$O·Al$_2$O$_3$·6.3SiO$_2$ and 0.76(NH$_4$)$_2$O·0.24K$_2$O·Al$_2$O$_3$·6.0SiO$_2$, respectively.

These ion-exchanged L-type zeolites were calcined at 540° C. for 3 hours under a circulation of air and the calcined products were molded into granular catalysts C, D, and E (105 to 250 μm) in the same manner as described in Example 1. The catalysts C, D, and E were subjected to the abrasion test, and by using these catalysts, chlorination of MCB was carried out in the liquid phase in the same manner as described in Example 1. The results obtained when 3 hours had passed from the initiation of chlorine gas blowing are shown in Table 2.

TABLE 2

|  | Example 2 | Example 3 | Example 4 |
|---|---|---|---|
| Catalyst[1] | C | D | E |
| Abrasion ratio (%) | 4.3 | 6.5 | 8.3 |
| Conversion (%) of MCB | 67.0 | 65.9 | 67.4 |
| Selectivity (%) to: | | | |
| PDCB | 90.0 | 87.1 | 82.9 |
| ODCB[2] | 9.2 | 11.9 | 16.2 |
| Others[3] | 0.8 | 1.0 | 0.9 |

Note
[1] Exchange ion site occupancy ratio of alkali metal cation: 100% (catalyst C), 67% (catalyst D), 24% (catalyst E)
[2] ODCB: ortho-dichlorobenzene
[3] Others: meta-dichlorobenzene and trichlorobenzenes

Examples 5 and 6

Granular zeolite catalysts F and G (105 and 250 μm) differing in the content of an L-type zeolite were prepared by using the L-type zeolite synthesized in Referential Example in the same manner as described in Example 1 except that the amount of the silica sol added was changed to 100 parts by weight or 200 parts by weight calculated as silica and distilled water was not added. The catalysts F and G were subjected to the abrasion test, and by using these catalysts, chlorination of MCB was carried out in the liquid phase in the same manner as described in Example 1. The results obtained when 3 hours has passed from the initiation of blowing of chlorine gas are shown in Table 3.

Comparative Example 2

A zeolite catalyst H having a particle size of 105 to 250 μm (105 to 177 μm: 65.6% by weight, 177 to 250 μm: 34.4% by weight) was prepared by using the L-type zeolite synthesized in Referential Example in the same manner as described in Example 1 except that the amount of the silica sol added was changed to 3 parts by weight calculated as silica and distilled water was added in an amount of 100 parts by weight. The catalyst H was subjected to the abrasion test, and by using this catalyst H, chlorination of MCB was carried out in the liquid phase in the same manner as described in Example 1. The results obtained when 3 hours had passed from the initiation of chlorine gas blowing are shown in Table 3.

Comparative Example 3

A homogeneous slurry was prepared by sufficiently mixing 5 parts by weight of the L-type zeolite synthesized in Referential Example with 100 parts by weight calculated as silica of silica sol, and a granular zeolite catalyst I (105 to 250 μm) was prepared from this slurry in the same manner as described in Example 1. The catalyst I was subjected to the abrasion test, and by using this catalyst I, chlorination of MCB was carried out in the liquid phase the same manner as described in Example 1. The results obtained when 3 hours had passed from the initiation of chlorine gas blowing are shown in Table 3.

TABLE 3

|  | Example 5 | Example 6 | Comparative Example 2 | Comparative Example 3 |
|---|---|---|---|---|
| Catalyst | F | G | H | I |
| Content (%) of L-type zeolite | 50.0 | 33.3 | 97.1 | 4.8 |
| Abrasion ratio (%) | 2.6 | 2.4 | 43.1 | 1.2 |
| Conversion (%) of MCB | 66.5 | 54.3 | 67.0 | 14.8 |
| Selectivity (%) to: | | | | |
| PDCB | 86.9 | 87.2 | 87.5 | 67.6 |
| ODCB[1] | 12.0 | 11.9 | 11.7 | 29.5 |
| Others[2] | 1.1 | 0.9 | 0.8 | 2.9 |

Note
[1] ODCB: ortho-dichlorobenzene
[2] Others: meta-dichlorobenzene and trichlorobenzenes

Example 7

The liquid phase chlorination of toluene was carried out in the same manner as described in Example 1 except that toluene was used instead of MCB. The results obtained when 3 hours had passed from the initiation of chlorine gas blowing are shown in Table 4.

Comparative Example 4

The liquid phase chlorination of toluene was carried out in the same manner as described in Comparative Example 1 except that toluene was used instead of MCB. The results when 3 hours had passed from the initiation of chlorine gas blowing are shown in Table 4.

TABLE 4

|  | Example 7 | Comparative Example 4 |
|---|---|---|
| Catalyst | A | B |
| Conversion (%) of toluene | 54.9 | 55.1 |
| Selectivity (%) to: | | |
| PCT[1] | 60.4 | 43.5 |
| OCT[2] | 33.9 | 47.1 |
| Others[3] | 6.7 | 9.4 |

Note
[1] PCT: para-chlorotoluene
[2] OCT: ortho-chlorotoluene
[3] Others: meta-chlorotoluene and dichlorotoluenes

Example 8

The continuous liquid phase chlorination of MCB was carried out by using the catalyst A prepared in Example 1. The reaction was conducted in a continuous reaction apparatus provided with an ordinary reaction vessel of the aeration suspension stirring tank type. More specifically, 265 g of MCB was charged in a reaction liquid overflow type Pyrex reaction vessel (inner diameter =50 mm, height =150 mm) having an inner capacity of about 300 ml and equipped with a gas introduction tube, a condenser, a stirrer and a catalyst separating and catalyst-circulating device, and 20 g of the catalyst A was suspended in MCB. Under sufficient agitation, chlorine gas was introduced at a feed rate of 440 ml/min and MCB was introduced at a rate of 266 g/hr by a pump. The reaction temperature was adjusted to 100° C. by controlling the temperature of the periphery of the reaction vessel by an oil bath. The change of the chlorine conversion with the lapse of time is shown in FIG. 1. The chlorine conversion is a value obtained by the following calculation:

Chlorine conversion (%) =

-continued $$\frac{\text{amount (mole) of chlorine supplied} - \text{amount (mole) of unreacted chlorine}}{\text{amount (mole) of chlorine supplied}}$$

During the reaction, a phenomenon that the catalyst powdered by abrasion flowed out from the catalyst-separating and catalyst-circulating device outside the reaction vessel together with the overflow liquid was not observed.

When 50 hours had passed from the initiation of the reaction, the zeolite catalyst was recovered by filtration, and the recovered catalyst was sufficiently washed with acetone, dried at 150° C. for 15 hours, and then calcined at 540° C. for 3 hours under a circulation of air. When the recovered catalyst was classified, it was found that the catalyst had the following particle size distribution:

below 74 μm: 3.4% by weight
74 to 105 μm: 0.6% by weight
105 to 177 μm: 47.9% by weight
177 to 250 μm: 48.1% by weight Comparative Example 5

The continuous liquid phase chlorination of MCB was carried out in the same manner as in Example 8 except that the catalyst H prepared in Comparative Example 2 was used. The change of the chlorine conversion with the lapse of time is shown in FIG. 1.

During the reaction, a phenomenon was observed that the catalyst powdered by abrasion flowed out from the catalyst-separating and catalyst-circulating device outside the reaction vessel together with the overflow liquid. Accordingly, the amount of the catalyst in the reaction vessel was reduced, and when 10 hours had passed from the initiation of the reaction, the chlorine conversion was abruptly reduced.

When 20 hours had passed from the initiation of the reaction, the catalyst in the reaction vessel was recovered and the recovered catalyst was combined with the catalyst which had flowed out from the reaction vessel. The combined catalyst was washed, dried, and calcined in the same manner as described in Example 8, and when the recovered catalyst was classified, it was found that the catalyst had the following particle size distribution:

below 74 μm: 89.5% by weight
74 to 105 μm: 7.3% by weight
105 to 177 μm: 2.1% by weight
177 to 250 μm: 1.1% by weight

We claim:

1. A process for preparing a parasubstituted halogenobenzene derivative selected from the group consisting of p-dichlorobenzene, p-dibromobenzene, p-diiodobenzene, p-chlorohalogenobenzene, p-bromohalogenobenzene, p-iodohalogenobenzene, p-chloroalkylbenzene, p-bromoalkylbenzene, and p-iodoalkylbenzene, wherein benzene, a monohalogenobenzene or a monoalkylbenzene is halogenated with a halogen selected from the group consisting of chlorine, bromine and iodine in the liquid phase in the presence of an L-type zeolite catalyst at a temperature of 0° C. to 200° C., said zeolite catalyst being a molded zeolite catalyst body which comprises, based on the weight of an L-type zeolite in the anhydrous state and 5 to 90% by weight of amorphous silica.

2. The process according to claim 1 wherein the L-type zeolite has a composition represented by the following oxide molar ratio formula:

$$xM_{2/n}O \cdot Al_2O_3 \cdot ySiO_2 \cdot zH_2O$$

wherein M is a cation, n is a valency of the cation M, x is a number of 0.7 to 1.3, y is a number of 4 to 8, and z is a number varying depending upon the extent of hydration of the zeolite and is from 0 to 9.

3. The process according to claim 2 wherein at least 30% of the cation M is an alkali metal cation.

4. The process according to claim 2 wherein at least 60% of the cation M is an alkali metal cation.

5. The process according to claim 1 wherein the zeolite catalyst comprises, based on the weight of the zeolite catalyst, 40 to 90% by weight of an L-type zeolite and 10 to 60% by weight of amorphous silica.

6. The process according to claim 1 wherein the amorphous silica is formed from a silica sol.

7. The process according to claim 1 wherein the molded zeolite catalyst body is calcined at a temperature of 300° C. to 900° C. before the use for the liquid phase halogenation.

8. The process according to claim 7 wherein the molded zeolite catalyst body is calcined for a period of 0.5 to 24 hours.

9. The process according to claim 1 wherein the monohalogenobenzene is mono-chlorobenzene and the monoalkylbenzene is toluene.

10. The process according to claim 1 wherein the liquid phase halogenation is carried out in a continuous manner while the benzene, monohalogenobenzene or monoalkylbenzene and a halogenating agent selected from the group consisting of chlorine, bromine and iodine are supplied at a rate of 0.5 to 300 1/kg-cat hour and 1 to 1500 mole/kg-cat hour, respectively.

11. The process according to claim 1 wherein the liquid phase halogenation is carried out in a batchwise or semi-batchwise manner using 0.001 to 1 kg of the molded zeolite catalyst body per liter of the reaction liquid.

12. The process according to claim 1 wherein the molded zeolite catalyst body used has an abrasion ratio of not more than 30% by weight.

* * * * *